US005643593A

United States Patent [19]
Fersch et al.

[11] Patent Number: 5,643,593
[45] Date of Patent: Jul. 1, 1997

[54] METHOD OF REDUCING CONTAINER RESIDUE OF WATER-DISPERSIBLE AGRICULTURAL CHEMICAL GRANULES BY WATER-SOLUBLE FILM COATING

[75] Inventors: Kenneth E. Fersch, Apex, N.C.; Arthur J. Miner, Barboursville, W. Va.

[73] Assignee: BASF Corporation, Mount Olive, N.J.

[21] Appl. No.: 527,918

[22] Filed: Sep. 14, 1995

Related U.S. Application Data

[62] Division of Ser. No. 241,894, May 13, 1994, Pat. No. 5,476,833.

[51] Int. Cl.⁶ ............................................. A01N 25/12
[52] U.S. Cl. ........................ 424/419; 424/417; 504/116; 504/247
[58] Field of Search ............................. 424/405, 409, 424/417, 419; 504/116, 247

[56] References Cited

U.S. PATENT DOCUMENTS

| | | | |
|---|---|---|---|
| 3,905,798 | 9/1975 | Zeeh et al. | 71/76 |
| 3,920,442 | 11/1975 | Albert et al. | 71/92 |
| 5,204,119 | 4/1993 | Shiobara et al. | 424/489 |
| 5,232,701 | 8/1993 | Ogawa et al. | 424/408 |
| 5,264,213 | 11/1993 | Shibahara et al. | 424/409 |
| 5,356,625 | 10/1994 | Ying | 424/94.1 |

FOREIGN PATENT DOCUMENTS

| | | | |
|---|---|---|---|
| 92107615.0 | 1/1994 | China | A01N 25/34 |
| 0 518 629 A1 | 12/1992 | European Pat. Off. | A01N 25/34 |
| 0 518 689 A1 | 12/1992 | European Pat. Off. | A01N 25/34 |
| 2 238 960 | 6/1991 | United Kingdom | A01N 25/12 |
| WO92/01374 | 2/1992 | WIPO | A01N 25/34 |
| WO92/01375 | 2/1992 | WIPO | A01N 25/34 |
| WO92/01376 | 2/1992 | WIPO | A01N 25/34 |
| WO92/01377 | 2/1992 | WIPO | A01N 25/34 |
| WO92/01378 | 2/1992 | WIPO | A01N 25/34 |
| WO92/17381 | 10/1992 | WIPO | B65D 65/46 |
| WO9217383 | 10/1992 | WIPO | B65D 77/04 |
| WO92/17385 | 10/1992 | WIPO | B65D 81/00 |

*Primary Examiner*—Neil S. Levy
*Attorney, Agent, or Firm*—Nixon & Vanderhye PC

[57] ABSTRACT

Water dispersible agricultural chemical formulations are disclosed wherein the individual granules are coated with a water-soluble film. The water-soluble film coating on the granules thus significantly reduces any chemical residue on interior surfaces of containers used to package the formulations for transport/handling, while it does not affect dispersibility of granules and providing the end-user with a variety of crop application rates—i.e., since the entire package does not need to be used. In preferred forms, the present invention is embodied in water dispersible agricultural chemical formulations wherein the water-soluble coating is polyvinyl alcohol, sodium silicate or an alkyl cellulose (e.g., methyl cellulose), of which, polyvinyl alcohol is particularly preferred.

7 Claims, No Drawings

METHOD OF REDUCING CONTAINER
RESIDUE OF WATER-DISPERSIBLE
AGRICULTURAL CHEMICAL GRANULES
BY WATER-SOLUBLE FILM COATING

This is a Divisional of application Ser. No. 08/241,894 filed on May, 13, 1994, (now U.S. Pat. No. 5,476,833).

RELATED APPLICATIONS

This application may be deemed to be related to commonly owned and copending U.S. application Ser. No. 07/968,926, U.S. Pat. No. 5,880,350 and U.S. Ser. No. 07/968,723 abandoned, each filed on Oct. 30, 1992, the entire content of each being incorporated expressly hereinto by reference.

FIELD OF INVENTION

The present invention relates to water-soluble film coating of water dispersible granules. In preferred forms, the present invention is embodied in water dispersible, dry flowable granules of agricultural chemicals (e.g., pesticides, plant growth regulators, insecticides, herbicides and the like) which are individually coated with a water-soluble film coating so as to effectively reduce/eliminate container residue, while at the same time not significantly adversely affecting the dispersibility characteristics of the granules.

BACKGROUND AND SUMMARY OF THE INVENTION

Dry, flowable, water-dispersible granular (hereinafter sometimes referred to as "WG") formulations of agricultural chemicals have achieved recent commercial popularity since they tend to be safer to apply and more environmentally friendly due to the ease by which such formulations may be handled. For examples, WG formulations of agricultural chemicals can eliminate the need for aromatic solvents thus reducing or eliminating volatile organic compounds. WG formulations also greatly reduce worker exposure to the chemical and usually reduce the overall toxicity of the formulations because of greatly reduced dust and aromatic solvents.

Furthermore, agricultural chemicals in the form of WG formulations will typically leave lesser residue on the interior surfaces of container packaging as compared to the same agricultural chemicals in the form of an emulsifiable concentrate or wettable powder. To eliminate all packaging residue, it has been proposed to provide water-dispersible granular formulations of agricultural chemicals in water-soluble bags so that the entire package (i.e., the water-soluble bag and the water-dispersible granules of agricultural chemicals contained therein) can simply be added to an appropriate amount of water prior to application. In this regard, please see International Application Nos. WO 92/17381 published on Oct. 15, 1992; WO 92/17385 published on Oct. 15, 1992; and WO 92/17383 published on Oct. 15, 1992, as well as European patent Application Nos. 0518629 A1 published on Dec. 16, 1992 and 0518689 A1 published on Dec. 16, 1992, the entire content of each such publication being incorporated expressly hereinto by reference. Agricultural chemicals in the form of water-dispersible gels which may or may not be contained within such water-soluble bags have been proposed as evidenced by International Application Nos. WO 92/01378; WO 92/01374; WO 92/01377; WO 92/10376 and WO 92/01375, the entire content of each such publication being incorporated expressly hereinto by reference.

Providing water-dispersible agricultural chemicals to the end users in a container system which is water-soluble is clearly advantageous in terms of reduced container residue—i.e., since no container physically remains after the agricultural chemical has been dispersed in water. However, providing WG agricultural chemicals pre-packaged in water-soluble containers has some disadvantages. For example, the water-soluble bag will sometimes break during transport and/or handling thereby completely nullifying any advantage in terms of chemical residue and/or reduced exposure which the bag was intended to provide. Furthermore, there is reduced flexibility in terms of chemical application rate since the entire water-soluble bag containing a pre-measured amount of the granular agricultural formulations is intended to be placed directly in water prior to application. That is, varying chemical application rates are very difficult to achieve by the user since the granular agricultural chemicals are packaged in pre-measured amounts which may not always meet the needs of the particular crop application. Furthermore, trace amounts of agricultural chemical can occur outside the water-soluble bag due to dust associated with commercial filling operations.

Therefore, what has been needed in this art is a suitable way to supply WG agricultural chemicals to the end user in a manner which significantly reduces (or eliminates entirely) chemical residue on interior surfaces of non-water-soluble containers while, at the same time, does not adversely affect the water-dispersibility property of the WG agricultural chemicals and provides the end-user with application rate flexibility. It is towards fulfilling such a need that the present invention is directed.

Broadly, the present invention is embodied in water dispersible agricultural chemical formulations wherein the individual granules are coated with a water-soluble film. The water-soluble film coating on the granules thus significantly reduces or eliminates any chemical residue on interior surfaces of containers used to package the formulations for transport/handling, while providing the end-user with a variety of crop application rates—i.e., since the entire package does not need to be used. A critical part of the present invention is that this coating is accomplished without significantly adversely affecting the dispersibility characteristics of the granules.

In preferred forms, the present invention is embodied in water dispersible agricultural chemical formulations wherein the water-soluble coating consists essentially of polyvinyl alcohol, sodium silicate, alkyl and hydroxyalkyl cellulose (e.g., methyl, propyl and ethyl cellulose and hydroxy methyl, hydroxypropyl and hydroxyethyl cellulose), polyethylene oxide, such as polyethylene glycol, starch and modified starch, carboxymethylcellulose, polyvinylethers such as polymethyl vinylether or poly(2-methoxyethoxyethylene), poly(2,4-dimethyl-6-triazinylethylene, poly(3-morpholinyl ethylene), poly(N-1, 2,4-triazolylethylene), poly(vinylsulfonic acid), polyanhydrides, low molecular weight melamineformaldehyde resins, low molecular weight urea-formaldehyde resins, poly(2-hydroxyethyl methacrylate), polyacrylic acid and its homologs. Most preferably, however, the water-soluble coating consists essentially of polyvinyl alcohol.

Further aspects and advantages of this invention will become more clear after careful consideration it given to the detailed description of the preferred exemplary embodiments thereof which follows.

DETAILED DESCRIPTION OF THE PREFERRED EXEMPLARY EMBODIMENTS

As used herein, and in the accompanying claims, the term "agricultural chemical" and like terms are meant to refer to pesticides, plant growth regulators (PGR's), insecticides, acaricides, nematocides, fungicides, miticides, herbicides, algicides, bactericides, mollusicides and the like. Thus, for example, an agricultural chemical useable in accordance with the present invention and classified as a PGR will exhibit one or more of the following plant responses: inhibition of cell elongation (e.g., reduction in stem height and internodal distance, strengthening of the stem wall thereby increasing the resistance of the plant to lodging); causing compact growth in ornamentals for the economic production of improved quality of plants; promoting better plant fruit bearing; increasing the number of ovaries with a view toward increased plant yield; promoting senescence of tissue formation, enabling fruit to absciss; defoliating nursery and ornamental bushes and trees for mail-order business during the fall season as well as to interrupt parasitic chains of infection; hastening ripening with a view toward programming the harvest by reducing the harvest to a minimal number of pickings; and interrupting the food-chain for injurious insects.

Preferred PGR's which may be employed in the practice of this invention include salts disclosed in U.S. Pat. No. 3,905,798, the entire content of which is expressly incorporated hereinto by reference. Preferred specific examples of such PGR's include 1,1-dimethyl-3,4-dehydropiperidinium bromide, 4-chloro-1,1-dimethyl-piperidinium bromide, 1,1-dimethyl-hexahydropyridazinium bromide, and 1,1-dimethyl-piperidinium chloride. The most preferred PGR is 1,1-dimethyl-piperidinium chloride, which is also known as N,N-dimethylpiperidinium chloride or mepiquate, and is commercially available under the registered trademark PIX® plant growth regulator from BASF Corporation.

Preferred herbicides include, for example, quinclorac (available commercially as FACET® agricultural chemicals from BASF Corporation), the sodium salt of bentazon (available commercially as BASAGRAN® herbicide from BASF Corporation), the sodium salt of acifluorifen (available commercially as BLAZER® herbicide from BASF Corporation), the sodium salt of sethoxydim, the dimethylamine salts of 2,4-D, difenzoquat methyl sulfate (commercially available as AVENGE® herbicide from American Cyanamid) and the like.

The coating material that may be employed in the present invention can be virtually any water-soluble material which is cable of being coated onto the surface of granular agricultural chemicals. For example, polyvinyl alcohol, sodium silicate and alkyl and hydroxyalkyl cellulose (e.g., methyl, propyl and ethyl cellulose and hydroxy methyl, hydroxypropyl and hydrox-yethyl cellulose) may be employed as the coating material. Furthermore, the coating material may be polyethylene oxide, such as polyethylene glycol, starch and modified starch, carboxymethylcellulose, polyvinylethers such as polymethyl vinylether or poly(2-methoxyethoxyethylene), poly(2,4-dimethyl-6-triazinylethylene, poly(3-morpholinyl ethylene), poly(N-1, 2,4-triazolylethylene), poly(vinylsulfonic acid), polyanhydrides, low molecular weight melamine-formaldehyde resins, low molecular weight urea-formaldehyde resins, poly(2-hydroxyethyl methacrylate), polyacrylic acid and its homologs.

Particularly preferred, however, is water soluble polyvinyl alcohol having a viscosity in the range of about 5.0 to about 20 cps (4% aqueous solution at 20° C.), and a percent hydrolysis (i.e., the percent acetate groups in the PVA which have been hydrolyzed) of greater than about 85%, and preferably between about 87% to about 99%. PVA that may be employed satisfactorily in the practice of this invention is commercially available, for example from Air Products Company under the tradename Airvol™ particularly preferred are Airvol™ 107 (viscosity of 5.5–6.6 cps/% hydrolysis of 98.0–98.8); Airvol™ 205 viscosity of 5.2–6.2 cps/% hydrolysis of 87.0–89.0); and Airvol™ WS-42 (viscosity of 14–17 cps/% hydrolysis of 96.5–97.5).

The water soluble coating material is applied onto the granular agricultural chemical by any suitable manner. For example, the water soluble coating material may be sprayed onto the granular agricultural chemical in the form of an aqueous coating solution containing between about 0.1 to about 20 wt. %, more preferably between about 1.0 to about 2.0 wt. % of the water soluble coating material. A bed of the granular agricultural material may itself be fluidized during the coating procedure by employing any suitable fluidized bed apparatus well known to those in the coating art.

The water soluble coating material is applied onto the surface of the individual granules of the agricultural chemical in an amount sufficient to significantly minimize (if not eliminate entirely) residue from adhering to the interior surfaces of containers which hold the chemicals, yet in an amount insufficient to affect significantly the ability of the agricultural chemicals to be dispersed in an aqueous solution. In this regard, it has been found that agricultural chemical residue on glass of less than about 4.0 ppm (and typically less than about 2.5 ppm) and a dispersibility index (DI) of between 1.0 to 2.0 comparable to uncoated water-dispersible granular agricultural chemicals can be achieved if the water-soluble coating material is present as a coating on the individual granules in an amount, based on the weight of the uncoated granular agricultural chemical, of between about 0.01 to about 1.0 wt. %, more preferably between about 0.04 to about 0.20 wt. %, and most preferably about 0.10 wt. %. As compared to uncoated granules of agricultural chemicals, the coated granules of agricultural chemicals according to the present invention will typically result in a decrease in container residue of between about 20–50 wt. % or more and especially a decrease of greater than about 75%.

The particle size of the agricultural chemicals employed in the practice of this invention is not particularly limiting. However, it is preferred that the particle size of the granular agricultural chemical be such that the granules pass through an 8 mesh screen but do not pass though a 40 mesh screen (US Standard Sieve). Thus, the granules should have an average particle diameter of greater than about 0.0165 inch.

The invention will be further illustrated by way of the following non-limiting Examples.

EXAMPLES

Dry flowable (DF) granules of water-dispersible quinclorac (75 wt. % FACET™ 75 DF (CAS # 84084-10-04) from BASF Corporation, hereinafter more simply referred to as "DF Granules") were coated with a selected one of a polyvinyl alcohol (PVA) resin identified as $PVA_1$ (Airvol™ 107, Air Products Company), $PVA_2$ (Airvol™ 205, Air Products Company), and $PVA_3$ (Airvol™ WS-42, Air Products Company) in the manner described below. The resulting PVA-coated granular quinclorac formulations were then tested for physical properties, including dispersibility, screen residue and container residue, in accordance with the procedures outlined below, with the results appearing in Table 1.

A. PVA Solution Preparation

The PVA resins that were used were not cold-water soluble. That is, for coating purposes, the PVA resins had to be dissolved in water by heating 4-liters of deionized water under constant stirring conditions to within 5° C. of the minimum cooking temperature ($T_{min}$) for the PVA resin used. Thus, the water was heated to 88° C. for $PVA_1$, 80° C. for $PVA_2$ and 86° C. for $PVA_3$. The PVA resin was then added to the stirred and heated water to give the desired amount of PVA in solution. The temperature of the PVA/$H_2O$ solution was then raised to $T_{min}$ and held at that temperature for 30 minutes. The solution was allowed to cool and make-up deionized water was added to the beaker to replenish any water that evaporated in the heating process.

B. PVA Coating of DF Granular Product

PVA-coated sample batches of DF Granules were made using a laboratory-size fluid-bed/spray-dryer unit (STREA-1 Aerocoat from Niro-Aermatic Company). Between 900–950 grams of DF Granules were used per sample batch. The DF Granules were constantly fluidized using a fan setting between 7–9 and coated with a fine mist of one of the PVA/$H_2O$ solutions described above using a spray nozzle placed below the container in which the DF Granules were fluidized. Atomization of the PVA/$H_2O$ solution was accomplished using a pressure of 2–4 bar and was sprayed onto the fluidized DF Granules at a rate of 10–12 grams per 10 seconds from a peristaltic pump. The PVA/$H_2O$ solution was sprayed onto the fluidized DF Granules in spray cycles of 10 seconds followed by 50 seconds of the pump being turned off. The spray cycles were repeated until the desired amount of PVA-coating on the DF Granules was achieved.

During spray-coating, the DF Granules were heated by 60° C. air which served to evaporate the excess water from the DF Granules. The liquid lines supplying the nozzle were emptied prior to terminating flow of the atomizing air so as to avoid any un-atomized PVA/$H_2O$ solution from entering the fluidized bed container. The coating process was terminated when the exit air temperature reached 50°–54° C., after which, the weight percent of PVA coated onto the DF Granules was determined by the formula $(PVA_{wt}/DFG_{wt})\times 100$, where $PVA_{wt}$ is the weight in grams of the PVA supplied to the nozzle (accounting for any PVA/$H_2O$ solution remaining in the solution fed line) and $DFG_{wt}$ is the weight in grams of the DF Granules.

C. Dispersibility Index (DI)

The number of inversion cycles of a cylinder containing 100 ml of water and approximately 2 grams of PVA-coated DF Granules from the sample batches prepared as described above was used to determine the dispersibility index (DI) as compared to uncoated DF Granules. In this regard, the DI was obtained by inverting the cylinder containing the PVA-coated DF Granules through 180° and then returning it to the original upright position for a total of five (5) such inversion cycles. After each five (5) inversion cycles, the cylinder was visually inspected to determine if the DF Granules had been dispersed in the water. If dispersion had not occurred, then cylinder was subject to an additional five (5) inversion cycles. The total number of inversion cycles was then divided by the total number of inversion cycles to disperse uncoated DF Granules to obtain the dispersion index (DI). A dispersion index (DI) of between 1.0–2.0 indicated comparable of not significantly different dispersibility to uncoated DF Granules, while values less than 1.0 or significantly greater than 2.0 indicated better or worse dispersibility, respectively, as compared to uncoated DF Granules.

D. Screen Residue

The screen residue is the amount of dispersed DF Granules retained on a 150μ sieve (100-mesh U.S. Sieve). Screen residue was determined using a test solution in which ten (10) grams of PVA-coated DF Granules were mixed with (3) liters of water. The solution was agitated for 15 minutes and then poured through a 100-mesh U.S. Sieve. The sieve was washed with six (6) liters of water at a rate of 1–1.5 liters per minute and then placed in a 54° C. incubator overnight to drive off any moisture. The amount of residue was determined by the weight gain of the mesh, with the screen residue (%) being determined by dividing the amount of residue by the initial sample weight and then multiplying by 100.

E. Container Residue

A 2-oz. glass bottle was filled with PVA-coated DF Granules and shaken vigorously for 5 minutes. The bottle was allowed to sit overnight and was then emptied. The emptied bottle was then rinsed thoroughly with 0.1-M NaOH which dissolved any residue on the interior bottle surfaces. A 1-ml aliquot of the residue solution was diluted with HPLC mobile phase and analyzed for the presence of quinclorac and expressed as parts per million (ppm) of the quinclorac in the residue solution. In Table 1 below, the container residue for the PVA-coated DF Granules was the average of two runs, whereas the container residue for the uncoated DF Granules was the average of nine runs.

TABLE 1

| Sample Batch No. | PVA Material | PVA Coating (wt. %) | PVA in Coating Solution (%) | Dispersibility Index (DI) | Screen Residue (%) | Container Residue (ppm) |
|---|---|---|---|---|---|---|
| Uncoated DF Granules | — | — | — | 1.0(3) | 0.001(1) | 6.09(2) |
| 1 | $PVA_1$ | 0.049 | 1.4 | ND | 0.005 | 2.09 |
| 2 | " | 0.061 | 1.4 | " | 0.009(3) | 3.09 |
| 3 | " | 0.086 | 1.4 | " | 0.034(3) | 2.02 |
| 4 | " | 0.100 | 1.4 | 0.8 | 0.045(3) | 1.48 |
| 5 | " | 0.150 | 1.4 | ND | 0.044 | 1.44 |
| 6 | $PVA_2$ | 0.035 | 1.0 | " | 0.399 | 1.12 |
| 7 | " | 0.059 | 2.0 | " | 0.499 | 2.81 |
| 8 | " | 0.060 | 2.0 | " | 0.522 | 3.24 |
| 9 | " | 0.078 | 1.0 | " | 2.016(3) | 1.46 |
| 10 | " | 0.101 | 2.0 | 0.8 | 0.678(3) | 2.75 |
| 11 | " | 0.156 | 2.0 | ND | 1.495(3) | 3.81 |
| 12 | $PVA_2$ | 0.202 | 2.0 | ND | 2.686(3) | 1.27 |
| 13 | $PVA_3$ | 0.036 | 1.0 | " | 2.807 | 2.27 |
| 14 | " | 0.054 | 1.0 | " | 4.203 | 1.94 |
| 15 | " | 0.076 | 1.0 | " | 6.083 | 2.56 |
| 16 | " | 0.102 | 1.0 | 1.0 | 7.928(3) | 1.13 |
| 17 | " | 0.122 | 1.0 | ND | 9.983(3) | 1.51 |

TABLE 1-continued

| Sample Batch No. | PVA Material | PVA Coating (wt. %) | PVA in Coating Solution (%) | Dispersibility Index (DI) | Screen Residue (%) | Container Residue (ppm) |
|---|---|---|---|---|---|---|
| 18 | " | 0.127 | 1.0 | " | 10.108[3] | 1.65 |
| 19 | " | 0.153 | 1.0 | " | 10.627 | 0.67 |
| 20 | " | 0.201 | 1.0 | " | 13.140[3] | 2.39 |

Notes:
[1]Average of three (3) runs.
[2]Obtained by disregarding an anomalous data point from one of the ten (10) inversion cycles, and averaging the remaining nine (9) data points.
[3]Average of two (2) runs.
ND — Not Determined As the data in Table 1 above demonstrate, water dispersible granular agricultural chemicals having a water-soluble coating on the individual granules in accordance with the present invention exhibit significantly reduced container residue as compared to uncoated granules of the same agricultural chemical. Furthermore, this reduced container residue property of the coated granules in accordance with the present invention is achieved without sacrificing the water-dispersibility characteristic of the granules.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of reducing container residue of a dry, flowable, granular, water-dispersible agricultural chemical comprising coating individual granules of the agricultural chemical with a layer of a water-soluble polyvinyl alcohol in an amount between about 0.01 to about 1.0 wt. %.

2. A method as in claim 1, wherein the granular agricultural chemical is fluidized and, wherein the water-soluble polyvinyl alcohol is sprayed onto the fluidized granular agricultural chemical so as to coat the individual granules thereof.

3. A method as in claim 1 or 2, wherein the water-soluble polyvinyl alcohol is sprayed onto the individual granules in the form of an aqueous solution containing between about 0.1 to about 20 wt. % of the water-soluble polyvinyl aalcohol.

4. A method as in claim 3, wherein the aqueous solution contains between about 1.0 to about 2.0 wt. % of the water-soluble polyvinyl alcohol.

5. A method as in claim 1, wherein the water-soluble coating layer polyvinyl alcohol is applied so as to be present on the individual granules in an amount between about 0.04 to about 0.20 wt. %.

6. A method as in claim 1, wherein the water-soluble coating layer polyvinyl alcohol is applied so as to be present on the individual granules in an amount of about 0.10 wt. %.

7. A method of reducing container residue of a dry, flowable, granular, water-dispersible quinclorac, comprising coating individual granules of the granular quinclorac with a layer of a water-soluble polyvinyl alcohol in an amount between about 0.01 to about 1.0 wt. % sufficient to prevent more than 4.0 ppm of the coated quinclorac granules from remaining as a residue on the interior surfaces of a container which contains the same.

* * * * *